United States Patent [19]

Witzel et al.

[11] 4,127,645
[45] Nov. 28, 1978

[54] EFFERVESCENT TABLET AND METHOD

[75] Inventors: Frank Witzel, Spring Valley; K. Warren Clark, Brewster, both of N.Y.

[73] Assignee: Life Savers, Inc., New York, N.Y.

[21] Appl. No.: 806,025

[22] Filed: Jun. 13, 1977

Related U.S. Application Data

[63] Continuation of Ser. No. 688,817, May 21, 1976, abandoned.

[51] Int. Cl.² .................. A61K 33/06; A61K 9/46; A61K 9/20
[52] U.S. Cl. ................................ 424/44; 424/16; 424/49; 424/154; 426/548; 426/591; 426/660
[58] Field of Search .................. 424/44, 48–58, 424/16, 154; 426/548, 591, 660

[56] References Cited

U.S. PATENT DOCUMENTS

| | | | |
|---|---|---|---|
| 207,013 | 8/1878 | Carter | 424/35 |
| 342,624 | 5/1886 | Michaelis | 426/591 |
| 543,601 | 7/1895 | Kerfoot | 424/44 |
| 1,262,888 | 4/1918 | Westlake | 424/44 |
| 1,765,867 | 6/1930 | Granger | 426/660 |
| 1,983,954 | 12/1934 | Taylor | 424/44 |
| 2,778,045 | 1/1957 | Bly et al. | 424/49 |
| 2,784,100 | 5/1957 | Endicott et al. | 426/548 |
| 2,803,551 | 8/1957 | Helgren | 426/548 |
| 3,012,893 | 12/1961 | Kremzner et al. | 426/591 |
| 3,061,445 | 10/1962 | Stanish | 426/548 |
| 3,098,749 | 7/1963 | Helgren | 426/548 |
| 3,151,028 | 9/1964 | Hay et al. | 424/55 |
| 3,433,644 | 3/1969 | Ganske et al. | 426/548 |
| 3,489,572 | 1/1970 | Kracauer | 426/591 |
| 3,667,962 | 6/1972 | Fritzberg | 426/591 |
| 3,677,770 | 7/1972 | Witzel | 426/548 |
| 3,908,003 | 9/1975 | Hersh | 424/32 |

FOREIGN PATENT DOCUMENTS

| | | |
|---|---|---|
| 2,989 of | 1883 | United Kingdom. |
| 9,100 of | 1891 | United Kingdom. |
| 12,503 of | 1894 | United Kingdom. |
| 21,535 of | 1901 | United Kingdom. |

OTHER PUBLICATIONS

Little et al., Tablet Making 2nd Ed. (1963) Northern Publ. Co., Liverpool, England, pp. 31 to 33, 61 to 66, 107–118, 139–140.

Primary Examiner—Shep K. Rose
Attorney, Agent, or Firm—Lawrence S. Levinson; Merle J. Smith; Burton Rodney

[57] ABSTRACT

An effervescent tablet, preferably in the form of a pressed tablet, useful in inhibiting or reducing dental plaque is provided, the tablet including a core portion containing an effervescent couple, and an outer portion which coats or surrounds the core portion, the outer portion containing a sugar alcohol, such as sorbitol. The effervescent tablet will preferably include a source of calcium ion to fortify teeth against demineralization. In addition, a method of inhibiting or reducing dental caries by use of the above described tablet as well as a method for protecting an effervescent couple from moisture absorption are also provided.

19 Claims, No Drawings

EFFERVESCENT TABLET AND METHOD

This is a continuation, of application Ser. No. 688,817, filed May 21, 1976, now abandoned.

The present invention relates to an effervescent tablet which is useful in reducing or inhibiting formation of dental plaque, which tablet includes a core portion containing an effervescent couple and an outer portion containing a sugar or sugar alcohol. In addition, the present invention relates to a method for using such tablet as well as a method for improving shelf life of a tablet containing an effervescent couple by coating the effervescent couple with a sugar or sugar alcohol.

The use of an effervescent couple in candies or tablets which interacts with water or aqueous medium to form carbon dioxide is well known. The liberated carbon dioxide imparts to the consumer the taste sensation associated with carbonated beverages and further imparts a cleansing action on tooth enamel. The problems associated with effervescent candy or tablets are twofold, namely, the off-taste due to unreacted food acidulant and the salt formed by reaction between the effervescent factors, for example sodium bicarbonate and an acidulant such as citric acid; the second problem resides in the limited shelf life of such a product due to rapid moisture absorption. Accordingly, an effervescent candy or tablet which overcomes the above disadvantages would be a welcomed addition to both the candy industry as well as those concerned with dental hygiene.

In accordance with the present invention, an effervescent tablet or candy is provided which includes a core portion and an outer portion or coating surrounding the core portion so as to prevent direct contact of the core portion with the surrounding atmosphere. The core portion includes an effervescent couple which comprises a leavening agent or basic material and an acidulant, and optionally includes one or more sweetening agents, and a source of calcium ion. The outer portion or coating is primarily formed of a sugar alcohol or sugar and may optionally include additional sweetening agents and a source of calcium ion. In preferred embodiments of the effervescent tablet or candy, both the core portion and the outer portion or coating will be primarily comprised of a sugar alcohol, such as sorbitol.

It has been found that the sugar alcohol or sugar in the coating or outer portion functions to shield the effervescent couple contained in the core portion from the surrounding atmosphere and thereby inhibits moisture absorption into the core. Furthermore, in accordance with the present invention it has been found that the off-taste due to unreacted acidulant in the effervescent couple as well as the salt formed by reaction between the effervescent factors to produce carbon dioxide can be pleasantly and effectively masked by including an acid or sour flavor in the outer portion or coating (which flavor is compatible with the acidulant of the effervescent couple) and including a non-acid or cream flavor in the core portion or coating which masks any salty taste present in the core. The acid flavor will provide a pleasant initial flavor which masks the initial unpleasant salty taste of the core and thus precoats or insulates the mount against a salty taste. Thereafter, the salty taste emanating from the core is masked by the non-acid or cream flavor. Thus, for example, the outer portion or coating can include an apple, lemon-lime, peach, strawberry, or other fruit-like flavor and the core portion may include a cream flavor such as vanilla, or other non-acid flavors such as maple, walnut, melon and the like.

The internal source of calcium ion will be present to prevent any possible demineralization of tooth enamel. The source of calcium ion may comprise calcium salts of long chain fatty carboxylic acids such as calcium stearate, calcium palmitate, calcium oleate and the synthetic sweetener calcium saccharin.

The effervescent couple employed herein will include an acidulant, such as an organic acid, for example, malic acid, fumaric acid, tartaric acid, citric acid, adipic acid, lactic acid, succinic acid, hexamic acid, or a corresponding anhydride, such as, citraconic anhydride, glucono-Δ-lactone, succinic anhydride, as well as acid salts, such as, potassium bitartrate, citrates and the like. In addition, the acid may comprise an inorganic acid, such as, sulfamic acid or a phosphoric acid as well as inorganic salts, such as, sodium aluminum sulfate, monocalcium phosphate and disodium pyrophosphate.

The leavening agent or basic material may comprise any of the metal carbonate salts, such as, alkali metal or alkaline earth metal carbonates and bicarbonates examples of which include lithium, sodium, potassium, magnesium and calcium carbonates or bicarbonates. A preferred effervescent couple comprises citric acid and sodium bicarbonate. Other effervescent couples particularly suitable for use herein comprise malic acid and sodium bicarbonate; potassium acid tartrate and sodium bicarbonate; glucono-Δ-lactone and sodium bicarbonate.

Each of the foregoing systems upon contact with water or aqueous medium form carbon dioxide, water and a salt.

Inasmuch as the tablet or candy of the invention is primarily desired for use as a dental hygiene product, it is preferred that the tablet or candy include sugar alcohols or synthetic sweeteners to provide the desired sweetness. In a preferred embodiment sugar alcohols, such as sorbitol, mannitol or xylitol will provide the desired sweetness level and will be included in both the outer portion or coating and the core. Other synthetic sweeteners may be employed in conjunction with or instead of the sugar alcohol in the coating and/or core. Examples of such synthetic sweeteners suitable for use herein include but are not limited to saccharin material, such as the free acid form of saccharin, saccharin salts, such as sodium or calcium saccharin, free cyclamic acid, cyclamate salts, L-aspartyl-L-phenylalanine methyl ester, dihydrochalcones, glycyrrhizin, glycyrrhizic acid ammonium salt, or mixtures of any of the above.

Where the effervescent tablet of the invention is to be employed primarily as a candy, it may include a sugar, such as sucrose, dextrose, glucose, fructose, lactose, maltose, and the like.

In formulating the effervescent tablet or candy of the invention, the core will be present in an amount within the range of from about 20 to about 80% by weight, and preferably from about 40 to about 60% by weight of the tablet or candy, and the coating or outer portion will be present in an amount within the range of from about 80 to about 20% by weight, and preferably from about 60 to about 40% by weight of the candy or tablet. The core portion will contain from about 10 to about 40% by weight of effervescent couple, and preferably from about 15 to about 30%; the core portion will optionally but preferably include a sugar alcohol sweetener present in an amount within the range of from about 50 to about 85% by weight and preferably from about 60 to about 80% by weight of the core; other sweeteners may be present in the core in amounts ranging from about 0.1 to about 20% and preferably from about 0.2 to about 5% by weight of the core. The source of calcium ion may also be present in the core in amounts ranging from about 0 to about 5% by weight and preferably from about 1 to about 3% by weight.

The outer portion or coating will be primarily composed of the sugar or sugar alcohol which will be present in amounts ranging from about 90 to about 99% by weight preferably from about 92 to about 95% by weight of the coating or outer portion; the coating or outer portion may optionally include additional sweetener in amounts ranging from about 0 to about 5% and preferably from about 0.1 to about 2% by weight of the coating or outer portion. The coating or outer portion may also optionally include the source of calcium ion in amounts within the range of from about 1 to about 5% and preferably from about 1 to about 3% by weight of the coating or outer portion.

In forming the effervescent tablet or candy of the invention, all ingredients to be employed including flavors, sweeteners and effervescent factors, are thoroughly blended. Spray dried flavors are preferably employed in the effervescent core to avoid initiation of the effervescent reaction.

The ingredients for the core portion are pressed and formed into a core. Thereafter the outer portion or coating material is applied as a dry coating to the core employing conventional punch and die equipment.

All blending, storage and tabletting procedures are carried out in a low humidity area, preferably at or below 40% relative humidity.

The following examples represent preferred embodiments of the present invention.

EXAMPLES 1-3

Double flavored dry coated effervescent tablets in accordance with the present invention having compositions set out in the following table are formed in accordance with the procedure set out below.

chine using a ⅜ inch flat faced bevel edged punch and die set at 17000 psi.

All of the above operations are carried out in an area having a controlled humidity of below about 40% relative humidity.

Each of the above naked tablets at 65-70% relative humidity has been found to have a shelf life of about 188 hours as compared to a shelf life of the core portion by itself of only 12 hours.

Upon sucking of the tablets in accordance with the present invention as shown in Examples 1-3, a pleasant acid or sour flavor is initially detected which slowly changes over to a pleasant non-sour flavor depending upon the particular non-sour flavor employed. The off-taste or salty taste of the core portion is effectively masked by the two flavors present in such tablets. The tablets of the invention are also found to be highly effective in inhibiting or reducing formation of dental plaque.

What is claimed is:

1. An effervescent candy comprising a core portion and an outer portion surrounding said core portion, said core portion comprising an effervescent couple including a leavening agent and an acidulant, said core portion further including a non-acid or cream flavor which masks the salty taste provided by the effervescent couple in the core portion, and said outer portion comprising a sugar or sugar alcohol and an acid or sour flavor compatible with said acidulant, which provides a pleasant initial flavor, and masks any salty taste emanating from said core.

2. The effervescent candy as defined in claim 1 wherein said core portion or said outer portion includes a source of calcium ion.

3. The effervescent candy as defined in claim 1 wherein said tablet includes a sweetener in addition to said sugar alcohol.

4. The effervescent candy as defined in claim 1 wherein said sweetener is a synthetic sweetener.

5. The effervescent candy as defined in claim 1 wherein said sweetener is selected from the group consisting of sodium saccharin, calcium saccharin, free acid form of saccharin, cyclamic acid, cyclamate salts, dihy-

| Formulations for Double Flavored Dry Coated Effervescent Tablets (Parts by Weight) | | | | | | |
|---|---|---|---|---|---|---|
| | Example 1 | | Example 2 | | Example 3 | |
| | Apple-Walnut | | Lemon-Lime-Watermelon | | Strawberries and Cream | |
| | Coating | Core | Coating | Core | Coating | Core |
| Sorbitol (tablet type) | 97 | 72 | 96 | 73 | 96 | 73 |
| Sodium Bicarbonate | | 16 | | 16 | | 16 |
| Citric Acid (Powdered) | | 8 | 1 | 8 | 0.75 | 8 |
| Calcium Stearate | 2 | 2 | 2 | 2 | 2 | 2 |
| Free Saccharin | 0.3 | 0.4 | 0.2 | 0.4 | 0.2 | 0.4 |
| Walnut Flavor | | 1 | | | | |
| Spray-dried Apple Flavor | 0.4 | | | | | |
| Spray-dried Lemon-lime Flavor | | | 1 | | | |
| Spray-Dried watermelon Flavor | | | | 0.5 | | |
| Strawberry Flavor | | | | | 0.9 | |
| Ground Spray Dried Vanilla Flavor | | | | | | 1 |

Each of the above effervescent tablets are formed by thoroughly blending in a standard ribbon or V-type blender the sorbitol, sodium bicarbonate citric acid, calcium stearate, free saccharin and flavor all of which are to be employed in the core portion. The core blend is then pressed at about 1000 psi with a ½ inch flat faced punch and die set. Thereafter, the coating ingredients, namely thoroughly blended sorbitol, calcium stearate, free saccharin and flavor are dried coated on the core portions employing a standard Manesty dry coat madrochalcones, L-aspartyl-L-phenylalanine methyl ester, glycyrrhizin, glycyrrhizic acid ammonium salt, or mixtures thereof.

6. The effervescent candy as defined in claim 1 wherein said core portion includes a sugar alcohol.

7. The effervescent candy as defined in claim 1 wherein said outer portion comprises a sugar alcohol.

8. The effervescent candy as defined in claim 7 wherein said sugar alcohol is selected from the group consisting of sorbitol, mannitol and xylitol.

9. The effervescent candy as defined in claim 8 wherein said sugar alcohol is sorbitol.

10. The effervescent candy as defined in claim 1 wherein said effervescent couple comprises an acidic material selected from the group consisting of acid, acid salts, and acidic anhydrides, and a basic material.

11. The effervescent candy as defined in claim 10 wherein said acidic material is a polycarboxylic acid or salt thereof and said basic material is a metal carbonate salt.

12. The effervescent candy as defined in claim 11 wherein said polycarboxylic acid is citric acid, or malic acid or tartaric acid and said metal carbonate is sodium bicarbonate.

13. The effervescent candy as defined in claim 14 wherein said effervescent couple comprises citric acid and sodium bicarbonate.

14. The effervescent candy as defined in claim 2 wherein said source of calcium ion comprises a calcium salt of a fatty carboxylic acid.

15. The effervescent candy as defined in claim 14 wherein said calcium salt comprises calcium stearate.

16. The effervescent candy as defined in claim 1 wherein said core portion comprises citric acid and sodium bicarbonate as the effervescent couple, sorbitol, saccharin and calcium stearate.

17. The effervescent candy as defined in claim 16 wherein said outer portion comprises sorbitol, calcium stearate and saccharin.

18. The effervescent candy as defined in claim 1 wherein said core portion comprises from about 20 to about 80% by weight of said tablet and said outer portion comprises from about 80 to about 20% by weight of said tablet.

19. The effervescent candy as defined in claim 18 wherein said tablet is a pressed tablet.

* * * * *